US008101802B2

(12) United States Patent
Groom et al.

(10) Patent No.: US 8,101,802 B2
(45) Date of Patent: Jan. 24, 2012

(54) ALLYLIC POLYSULFANES

(75) Inventors: Murree Groom, Thetford (GB); Eric Block, Niskayuna, NY (US)

(73) Assignee: ECOspray Limited, Norfolk (GB)

( * ) Notice: Subject to any disclaimer, the term of this patent is extended or adjusted under 35 U.S.C. 154(b) by 271 days.

(21) Appl. No.: 12/514,370

(22) PCT Filed: Nov. 12, 2007

(86) PCT No.: PCT/GB2007/004310
§ 371 (c)(1),
(2), (4) Date: May 11, 2009

(87) PCT Pub. No.: WO2008/059217
PCT Pub. Date: May 22, 2008

(65) Prior Publication Data
US 2010/0274037 A1    Oct. 28, 2010

(30) Foreign Application Priority Data

Nov. 11, 2006 (GB) .................................. 0622549.4
Jun. 12, 2007 (GB) .................................. 0711308.7

(51) Int. Cl.
*C07C 321/00* (2006.01)
*C07C 323/00* (2006.01)
(52) U.S. Cl. ................ 568/21; 568/22; 568/24; 568/25; 556/428
(58) Field of Classification Search ............... 568/21, 568/22, 24, 25; 556/428
See application file for complete search history.

(56) References Cited

U.S. PATENT DOCUMENTS

| 4,551,259 | A | 11/1985 | Milton |
| 6,511,674 | B1 | 1/2003 | Arand et al. |
| 2002/0198410 | A1 | 12/2002 | Sinha et al. |
| 2004/0265702 | A1 | 12/2004 | Kim |
| 2005/0079095 | A1 | 4/2005 | Crovetto et al. |

FOREIGN PATENT DOCUMENTS

| BE | 903756 | 12/1985 |
| CN | 1565430 | 1/2005 |
| CN | 1985591 | 6/2007 |
| EP | 0464521 | 6/1991 |
| FR | 2863144 | 6/2005 |
| GB | 2414912 | 12/2005 |
| HU | 9700287 | 11/1998 |
| HU | 9802619 | 6/2000 |
| IN | 144278 | 4/1978 |
| JP | 7-126108 | 5/1995 |
| JP | 11-222410 | 8/1999 |
| JP | 2007-261983 | 10/2007 |
| KR | 1007864619 | 12/2007 |

OTHER PUBLICATIONS

N. Yamada, et al.: "Direct preparation of anhydrous sodium oligo sulphides from metal sodium and elemental sulphur in aprotic media directed toward synthesis of silane coupling agent", Chemistry Society of Japan, Chemistry Letters No. 4, Apr. 2002, pp. 454-455, ISSN: 0366-7022, figure 2, 4$^{th}$ entry.
R.C. Fuson et al.: ":Levinstein mustard gas. IV. The bis-(2-chloroethyl) polysulphides", Journal of Organic Chemistry, vol. 11, No. 5, Sep. 1946, pp. 487-498, American Chemical Society, Washington, DC, US, ISSN: 0022-3263, p. 493, last paragraph.
T. Ariga et al., "Chemical synthesis of allyl methyl trisulphide. A component of garlic oil", No. 42, 1985, pp. 68-74.
M. Born et al., "Structure chimique et proprieties extreme-pression de sulfures et de polysulfures organiques", Journal de Chimie Physique., vol. 97, No. 84, 2002, pp. 315-324.
Sulfur Letters, "Preparation De Sulfures β-Ethyleniques; Role Du Soufre Dans Leurs Spectres De Masse", vol. 2(3), 1984, pp. 77-80.
Sulfur Letters, "Etude De Sulfures, Sulfoxydes Et Sulfones En RMN C13, Determinations D'Increments Pour Ces Fonctions.", vol. 8(1), 1988, pp. 27-30.
Sulfur Letters, "Etude Par Spectrometrie De Masse De Polysulfures", vol. 9(1-2), 1989, pp. 17-21.
"Zhurnal Organicheskoi Khimii", Chemical Abstracts, 1967.
"Zhurnal Prikladnoi Khimii", Chemical Abstracts, 1986.
A. Kuznetsov et. al., "Reaction of 4,4'-Dithiobis(2,6-di-*tert*-butylphenol) with Sulfur Containing Its Polymeric Modification" Russian Journal of General Chemistry, vol. 71, No. 4, 2001, pp. 657-658.
United Kingdom search report for corresponding application No. GB0722185.6 dated Mar. 11, 2008.
U. Münchberg et al., "Polysulfides as biologically active ingredients in garlic" Org. Biol. Chem., Mar. 14, 2007, pp. 1505-1518.
T. Hosono et al., "Diallyl trisulfide suppresses the proliferation and induces apoptosis of human colon cancer cells through oxidative modification of β-tubulin", Biol. Chem, Oct. 11, 2005, pp. 41487-41493.
P. Sinha et al., Copper(II)/Tin(II) Reagent for Allylation, Propargylation, Alkylation, and Benzylation of Disulfides and Elemental Sulfur: New Insight into the "Copper Effect", Organometallics, vol. 20, No. 1, 2001, pp. 157-162.
Y. Chu et al., "Synthesis of diallyl mono-and polysulfides", West China University of Medical Sciences, 2001, Abstract only.
B. Milligan et al., "Trisulphides and Tetrasulphides from Bunte Salts", Journal of the Chemical Society, 1963, pp. 3608-3614.
M. L. Selker, "Sulfur Linkage in Vulcanized Rubber", Reaction of Methyl Iodide with Sulfur Compounds, Bell Telephone Laboratories, Journal of Industrial and Engineering Chemistry, 1948, pp. 1467-1470.
J. S. Thomas et al., "Organic polysulfides. II. The action of anhydrous potassium pentasulfide on allyl iodide and on some aromatic halogen compounds", Journal of the Chemical Society, 1924, pp. 2214-2219.
G. Höfle et al., "Thiosulfoxides. The intermediates in rearrangement and reduction of allylic disulfides", Journal of the Chemical Society, 1971, pp. 6307-6308.

(Continued)

*Primary Examiner* — Porfirio Nazario Gonzalez
(74) *Attorney, Agent, or Firm* — Renner, Otto, Boisselle & Sklar, LLP

(57) ABSTRACT

Diallylic polysulfides (polysulfanes) are provided with sulfur chain lengths of 9 to 22. Also provided are bis(2-methyl-2-propenyl) polysulfides with sulfur chain lengths of 3 to 22. Also provided are 2-substituted bis(2-propenyl) polysulfides with sulfur chain lengths of 3 to 20. Also provided are the 2-cycloalken-1-yl polysulfides, 2-cyclohexen-1-yl polysulfides and 2-cyclopenten-1-yl polysulfides, with sulfur chain lengths of 3 to 20. Also provided are processes for extending the sulfur chain length of diallylic polysulfides and 2-substituted analogues thereof and allyl methyl polysulfides by bringing such compounds into contact with elemental sulfur and heating, or by mixing with molten sulfur.

15 Claims, 4 Drawing Sheets

OTHER PUBLICATIONS

R. Steudel et al., "Sulphur compounds. Part 140. Structures and relative stabilities of seven isomeric forms of H2S2O2", Journal of Chemical Society, 1991, pp. 2395-2399.

D. Grant et al., Exchange of parts between molecules at equilibrium. V. Alkyl-terminated chain polysulfides and polyselenides, Journal of the American Chemical Society, 1964, pp. 3012-3017.

R. B. Baechler et al., "Reaction of allylic thioethers with elemental sulfur", Journal of the American Chemical Society, 1973, pp. 4442-4444.

R. Steudel et al., "Sulfur compounds, 212. Preparation of organic polysulfanes R2Sn (n=5,7,8,9) from sulfenyl chlorides, RSCI, and transition metal polysulfido complexes", Journal of European Inorganic Chemistry, 2000, 921-928.

A. G. Hile et al., "Aversion of Eurpean starlings (Sturnus vulgaris) to garlic oil treated granules: Garlic oil as an avian repellent. Garlic oil analysis by nuclear magnetic resonance spectroscopy", Journal of Agricultural and Food Chemistry, 2004, pp. 2192-2196.

ALLYLIC POLYSULFANES

This application is a national phase of International Application No. PCT/GB2007/004310 filed Nov. 12, 2007 and published in the English language.

FIELD OF THE INVENTION

The invention relates to new diallylic polysulfanes and substituted analogues thereof; methods for producing such compounds; and methods for extending the sulfur chain length of polysulfanes.

BACKGROUND AND PRIOR ART KNOWN TO THE APPLICANT

Diallyl polysulfides (polysulfanes: DASn, where n≧2) and derivatives thereof are found naturally, e.g., in garlic oil (distilled oil of garlic), and have found use in a number of areas of technology, for example as pesticides. It is known that the biological activity of the diallyl polysulfides varies with sulfur chain length, with longer chain length molecules often showing increased activity (1). Within the family of diallyl polysulfides occurring naturally, molecules with more than eight sulfur atoms are unknown. It is expected, however, that these would find enormous potential, and show enhanced or alternative properties to those of known diallyl polysulfides.

As a mark of the potential applications of diallyl polysulfides, some examples of application areas are outlined below, with reference to other published literature and patent applications:

DAS2 and DAS3 (diallyl disulfide and diallyl trisulfide) may be used as nematicides to control pine wood nematodes without side effects to the environment such as the reduction of populations of beneficial organisms, development of tolerance through enhanced degradation and resistance, and through toxicological disturbance to ecosystems that encourage outbreaks of latent insect infestations and induction of toxicity to human and domestic animals (2); DAS2-DAS7 (diallyl disulfide through diallyl heptasulfide) may be used as insecticides, acaricides, virucides, fungicides and plant growth regulators (3, 4); diallyl polysulfides may be used as stabilizers and polymerization inhibitors for unsaturated compounds and as antioxidant components (5); they may be used as pesticides for foliar application and other agricultural uses (6-8) and as tickicides (9); DAS2-DAS4 (diallyl disulfide through diallyl tetrasulfide) may be used for prevention of pine-wilt disease by controlling larvae of *Bursaphelenchus xylophilus* (10); they may be used as plant dormancy-inhibiting agents to accelerate budding (11); diallyl polysulfides may be used as optical materials having increased refractive index, as extreme-pressure additive and lubricating oil compound for automotive transmissions, and as protective electrolytes for lithium batteries (12); they may be used as amine-free corrosion inhibitors (13); in the form of cyclodextrin inclusion compounds they may be used as therapeutic agents (14); DAS3-DAS7 may be used as fungicides and lipid peroxidation inhibitors (15); diallyl polysulfides may be used as food preservatives and browning inhibitors (16).

There are also reports in the scientific literature on the use of diallyl trisulfide and tetrasulfide as antibiotics, antimicrobials, antithrombotic agents, antiparasitic agents, apoptosis-inducers and antitumor agents, anti-angiogenesis agents, and as compounds offering protection against toxicity caused by cadmium and other toxic metals. It can be seen that the range of applications is wide, and higher chain-length diallyl polysulfides would have utility in a number of technical fields.

Processes for the production of diallyl trisulfide, tetrasulfide and pentasulfide are known (17-24).

SUMMARY OF THE INVENTION

Accordingly, the invention provides, in a first aspect, a compound of formula:

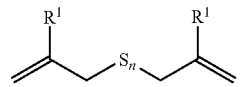

where n is from 3 to 22; and
$R^1$ is selected from the group comprising:
  hydrogen;
  methyl;
  phenyl;
  carboethoxy;
  carbomethoxy;
  carboxy;
  hydroxymethyl;
  trimethylsilylmethyl;
  short-chain alkyl;
  chloro; and
  fluoro;
provided that when n is from 3 to 8, $R^1$ is not hydrogen.

In particular, the invention provides such compounds where n is greater than or equal to 4, or 5, or 6, or 7, or 8, or 9, or 10, or 11, or 12, or 13, or 14, or 15, or 16, or 17, or 18 whilst n is less than, or equal to 21, 20, or 19. For example, n is from 4 to 22, or 5 to 22, or 6 to 22, etc.; or from 4 to 21, or 5 to 21, or 6 to 21, or 7 to 21, etc.; or from 4 to 20, or 5 to 20, or 6 to 20, or 7 to 20 etc.

In particular also, it is preferred that when n is from 3 to 9, or from 3 to 10, or even from 3 to 11, $R^1$ is not hydrogen.

Within this group, said short chain alkyl groups preferably comprise alkyl groups with 2, 3, or 4 carbon atoms.

In a second aspect, the invention provides a compound of formula:

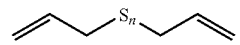

where n is from 9 to 22. In particular, the invention provides such compounds where n is greater than or equal to 10, or 11, or 12, or 13, or 14, or 15, or 16, or 17, or 18 whilst n is less than, or equal to 21, 20, or 19. For example, n is from 4 to 22, or 5 to 22, or 6 to 22, etc.; or from 4 to 21, or 5 to 21, or 6 to 21, or 7 to 21, etc.; or from 4 to 20, or 5 to 20, or 6 to 20, or 7 to 20 etc.

In a third aspect, the invention also provides a compound of formula:

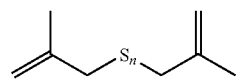

where n is from 3 to 22. In particular, the invention provides such compounds where n is greater than or equal to 4, or 5, or 6, or 7, or 8, or 9, 10, or 11, or 12, or 13, or 14, or 15, or 16, or 17, or 18 whilst n is less than, or equal to 21, 20, or 19. For example, n is from 4 to 22, or 5 to 22, or 6 to 22, etc.; or from 4 to 21, or 5 to 21, or 6 to 21, or 7 to 21, etc.; or from 4 to 20, or 5 to 20, or 6 to 20, or 7 to 20 etc.

In a fourth aspect, the invention also provides a process for extending the sulfur chain length of diallylic polysulfides selected from the group comprising:

bis(2-propenyl) polysulfides; and 2-substituted bis(2-propenyl) polysulfides;

comprising the steps of mixing said diallylic polysulfide with elemental sulfur and heating the mixture to a temperature in excess of 50° Celsius. Reaction rates and yields increase with increasing temperatures, and markedly so, and it is therefore particularly preferred that the mixture is heated to a temperature in excess of 60° C., or in excess 70° C., or in excess 80° C., or most preferably in excess 90° C. In especially preferred embodiments, said mixture is heated to a temperature at or around, or even in excess of the melting point of elemental sulfur (115-120° C.). In especially preferred embodiments, the process comprises extending the sulfur chain length of diallyl disulfide to produce diallyl polysulfides containing between 3 and 8 sulfur atoms, by such a reaction with elemental sulfur.

In a fifth aspect, the invention also provides a process for extending the sulfur chain length of diallylic polysulfides selected from the group comprising:

bis(2-propenyl) polysulfides; and 2-substituted bis(2-propenyl) polysulfides;

said process comprising the steps of mixing said diallylic polysulfide with molten sulfur.

Within said fourth and fifth aspects, it is preferable that said diallylic polysulfide comprises diallyl disulfide, i.e. bis(2-propenyl) disulfide.

In the fourth or fifth aspects of the invention, it is particularly preferred that said diallylic polysulfides so produced comprise polysulfides having fewer than 22 sulfur atoms.

In a sixth aspect, the invention also provides a compound of formula:

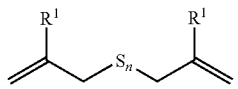

where $R^1$ is selected from the group comprising:

phenyl;

carboethoxy;

carbomethoxy;

carboxy;

hydroxymethyl;

short-chain alkyl;

trimethylsilylmethyl;

chloro; and fluoro;

and n is from 3 to 20.

Within this group, said short chain alkyl groups preferably comprise alkyl groups with 2, 3, or 4 carbon atoms.

In a seventh aspect, the invention also provides a compound of formula:

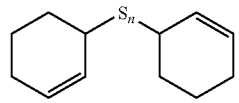

where n is from 3 to 20.

In preferred embodiments, n is from 3 to 18.

The invention also provides a compound of the formula:

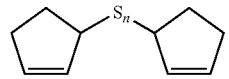

where n is from 3 to 20.

In preferred embodiments, n is from 3 to 18.

In an eighth aspect, the invention also provides a process for extending the sulfur chain length of allyl methyl polysulfides ($MeS_nCH_2CH=CH_2$) comprising the steps of mixing said allyl methyl polysulfide(s) with elemental sulfur and heating the mixture to a temperature in excess of 50° Celsius. Reaction rates and yields increase with increasing temperatures, and markedly so, and it is therefore particularly preferred that the mixture is heated to a temperature in excess of 60° C., or in excess 70° C., or in excess 80° C., or most preferably in excess 90° C. In especially preferred embodiments, said mixture is heated to a temperature at or around, or even in excess of the melting point of elemental sulfur.

In a ninth aspect, the invention also provides a process for extending the sulfur chain length of allyl methyl polysulfides ($MeS_nCH_2CH=CH_2$) comprising the step of mixing said allyl methyl polysulfides with molten sulfur.

In any of the processes described in the fourth, fifth, eighth or ninth aspects, it is particularly preferred that the reaction is undertaken substantially free of additional solvents.

Also in any of the processes described in the fourth, fifth, eighth or ninth aspects, individual polysulfanes so produced may be obtained by separation methods such as preparative high performance liquid chromatography (HPLC) while separation into mixtures of lower polysulfides and mixtures of higher polysulfides can be achieved by extraction with methanol or ethanol. The higher polysulfanes (e.g. with S chain lengths greater than approximately $S_7$) are insoluble in alcohols, especially methanol. Alternatively, the mixtures of sulfur chain length homologues so produced may be used in combination, as required.

Also in any of the processes described in the fourth, fifth, eighth or ninth aspects, a single homologue starting material may be used (such as diallyl disulfide, for example) or a pre-existing mixture may be used, such as a natural extract, or distillate, from garlic (*Allium sativum*).

Significant and unique features of the present invention include high reactions rates requiring very short heating times, excellent yields, avoidance of solvents, lack of odour of the higher polysulfides, and formation of polysulfides containing up to twenty chain sulfur atoms, e.g. $All_2S_n$, where n equals each whole number from 1 to 20. The diallylic higher polysulfides are novel materials, not previously known (above $All_2S_8$, in the case of the parent diallyl system), which are nonpolar and soluble in chloroform and related solvents but are insoluble in alcohols, in contrast to lower diallylic polysulfides.

Also included within the scope of the invention are compounds and processes substantially as described herein, with reference to and as illustrated by any appropriate combination of the accompanying drawings.

DESCRIPTION OF PREFERRED EMBODIMENTS

Figure 1:
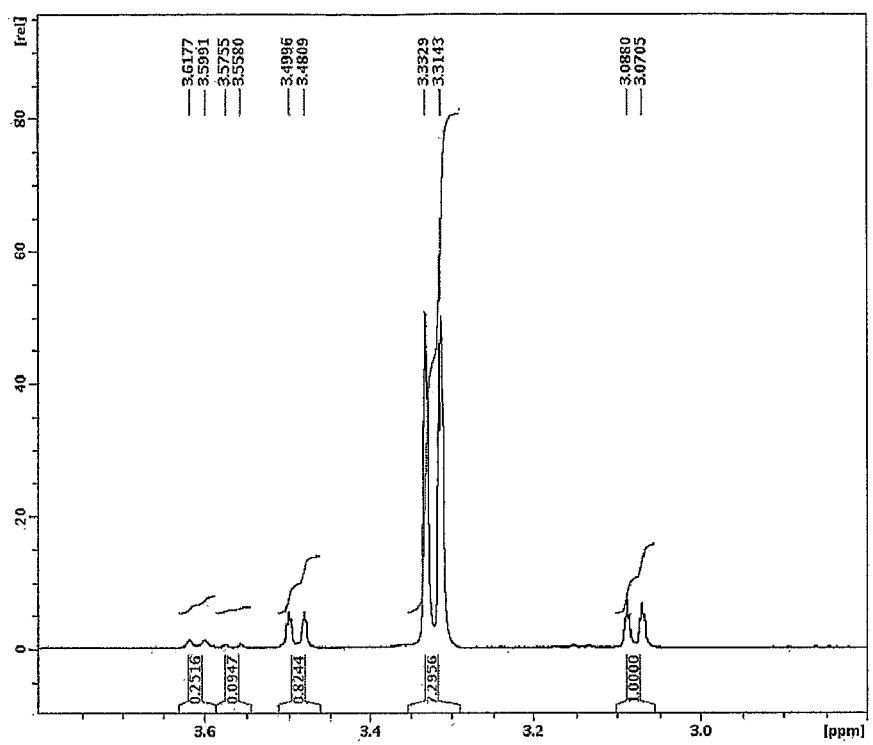
FIG. 1 is a graph of a NMR spectrum of a starting material described in Example 1.

Diallyl disulfide is added with vigorous stirring to sulfur which has been liquefied at its melting temperature of 115-120° C. The ratio of diallyl disulfide to sulfur (as $S_8$) can range from 1:0.25 to 1:2 although smaller and larger ratios than those specified can be used. The rate of the reaction at 120° C. is faster when disulfide:sulfur ratio decreases (e.g., $S_8$>disulfide). Substantial reaction occurs as soon as five minutes and is virtually complete after two hours. At 115° C. the reaction of diallyl disulfide and liquid sulfur is slower. At temperatures above 120° C. the reaction is faster but decomposition occurs, as indicated by significant darkening of the reaction mixture.

With saturated disulfides, such as dibenzyl disulfide, lacking allylic groups on sulfur the reaction is substantially slower and is thought to occur by a different mechanism. Diallyl sulfide also reacts with liquid sulfur substantially slower than diallyl disulfide so a different mechanism must be involved in this case as well. The reaction with sulfur also occurs with substituted diallylic disulfides such as bis(2-methylallyl) disulfide but not with bis-cinnamyl disulfide, e.g., $(PhCH=CHCH_2S)_2$, where conjugation would be destroyed in the postulated thiosulfoxide intermediate, e.g., $CH_2=CHCH(Ph)S(S)CH_2CH=CHPh$. Any 2-substituted diallylic disulfide should undergo the reaction, bis(2-phenyl-2-propenyl), bis(2-carboethoxy-2-propenyl), bis(2-carbomethoxy-2-propenyl), bis(2-carboxy-2-propenyl), bis(2-hydroxymethyl-2-propenyl), bis(2-chloro-2-propenyl), bis (2-fluoro-2-propenyl) or bis(2-trimethylsilylmethyl) disulfide. Other diallylic disulfides which should undergo the reaction are 2-cycloalken-1-yl disulfides, e.g., 2-cyclohexen-1-yl and 2-cyclopenten-1-yl disulfides, which can be considered 1,3-disubstituted diallylic disulfides. In each of the above cases the starting materials would be the mentioned disulfide and an amount of $S_8$ ranging from 0.25 to 2 equivalents and the reaction conditions would involve heating from 115° C. to 120° C. for up to three hours. While the above incorporates optimum conditions, the range of the ratio of $S_8$ as well as the temperature of heating and time period of heating could be broader than those described.

The reaction is believed to involve isomerization of the diallylic disulfide, e.g., All-SS-All, to the thiosulfoxide isomer, e.g., $All_2S^+—S^-$ (25). The thiosulfoxide group is a polar group, with the terminal sulfur bearing a negative charge (25, 26), and this negatively charged sulfur is postulated to attack and ring-open cyclooctasulfur, $S_8$, giving an ionic species, e.g. $All_2S^+—S_8—S^-$, which attacks (most likely by an $S_N2'$ process) the starting diallylic disulfide through the negatively charged sulfur giving terminal thioallylated product, e.g., $All_2S^+—S_8—SAll$, which then loses one of the two allylic groups attached to the positive thiosulfonium sulfur through attack of a nucleophile giving a product of type $AllS—S_8—SAll$. This product can then lose various numbers of sulfur atoms as small molecules S. The overall process is clearly quite different from the reaction of saturated disulfides with cyclooctasulfur, which only occurs at higher temperatures and is believed to involve free radical ring opening of the cyclooctasulfur giving diradicals such as ●S● and free radical cleavage of the disulfide, giving radicals such as RS●(27). The higher temperature and free radical nature of reactions involving saturated disulfides would limit formation of the unstable and reactive higher polysulfides, whose presence in our work is confirmed by reversed phase HPLC analysis and mass spectrometry. By the same token diallyl sulfide, $All_2S$, lacks the polar $S^+—S^-$ bond to enhance ring opening of $S_8$. Thus attack by the much less nucleophilic sulfide sulfur of $All_2S$ on $S_8$ would also require more vigorous, higher temperature conditions (28). When liquid $S_8$ and $All_2S$ in the molar ratio of 0.625 to 1 were heated at 120° C. for two hours no reaction was observed.

Example 1

Diallyl Disulfide and Elemental Sulfur (as $S_8$) in a 1:1 Molar Ratio

Figure 2:
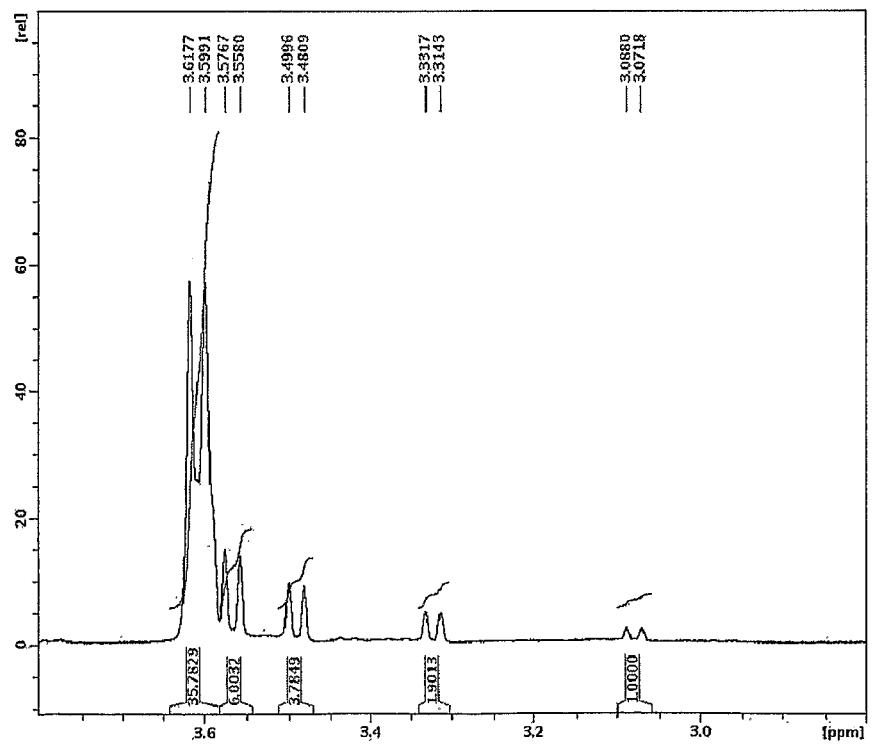
FIG. 2 is a graph of a NMR spectrum of a hr sample described in Example 1.

A 10 mL round-bottomed flask containing sublimed sulfur ($S_8$, 0.640 g, 2.50 mmol) was placed in an oil bath pre-heated to 120° C. When all of the sulfur had melted into a clear, straw-coloured liquid, diallyl disulfide (0.365 g, 2.50 mmol) was added all at once to the magnetically stirred liquid. Within three minutes, the initial cloudy two-layer liquid mixture became a clear, homogeneous solution with only one liquid layer. A small amount of sample was withdrawn from the reaction mixture for analysis at various time points, e.g. 5 min, 30 min, 1 h, 1.5 h, and 2 h. The withdrawn samples were dissolved in $CDCl_3$ permitting both NMR and reversed phase HPLC analysis to be performed on the same sample. As desired, the remaining material could be directly used or the methanol- or ethanol-soluble fraction separated by extraction from the alcohol insoluble residue, which could then be dissolved in chloroform for further use. Analysis of a sample, dissolved in $CHCl_3$, by C18 HPLC (85:15 $MeOH:H_2O$) showed a series of evenly spaced peaks corresponding to $(CH_2=CHCH_2)_2S_n$, n=2-20, along with unreacted $S_8$, as shown in the attached HPLC trace. Diode-array UV spectra of each HPLC peak supported the "family" relationship of members of the mixture. Our observations are consistent with HPLC studies of families of dialkyl polysulfanes where a linear relationship exists between the number of sulfur atoms in the chain and the natural logarithm of the capacity factor, calculated from the retention time (29). Comparison of the [1]NMR spectrum of the starting material (FIG. 1) with the 1 hr sample (FIG. 2) clearly shows the appearance of a doublet for the $CH_2—S$ protons at δ 3.62 and 3.60, characteristic of $All_2S_n$, n≧5.

NMR analysis of diallylic polysulfides can be used to quantify the relative amounts of monosulfide, disulfide, trisulfide, tetrasulfide and combined pentasulfides and higher polysulfides due to the progressive deshielding of the $CH_2S_n$ protons (30).

The HPLC analysis was as follows:

| Retention Time (min) | Peak Area (% Total) | Peak Identity |
|---|---|---|
| 3.9 | 1.4 | DAS2 |
| 5.1 | 1.9 | DAS3 |
| 6.8 | 4.0 | DAS4 |
| 9.4 | 6.4 | DAS5 |
| 13.7 | 9.3 | DAS6 |
| 19.9 | 8.8 | DAS7 |
| 23.8 | — | $S_8$ |
| 29.1 | 8.6 | DAS8 |
| 39.7 | 8.4 | DAS9 |
| 50.3 | 7.8 | DAS10 |
| 59.3 | 7.1 | DAS11 |
| 66.8 | 6.3 | DAS12 |
| 73.8 | 5.7 | DAS13 |
| 80.8 | 5.2 | DAS14 |
| 87.5 | 4.3 | DAS15 |
| 94.1 | 3.8 | DAS16 |
| 101.2 | 3.1 | DAS17 |
| 109.7 | 2.7 | DAS18 |
| 120.0 | 2.3 | DAS19 |
| 132.8 | 1.6 | DAS20 |
| 148.6 | 1.3 | DAS21 |

Data from $^1$H NMR analysis at 500 MHz (relative to internal standard) showing the percentage of each homologue produced over time is given below:

| Time | DAS1 | DAS2 | DAS3 | DAS4 | $\geq$DAS5 |
|---|---|---|---|---|---|
| 0 min | 11.0% | 80.0% | 9.0% | — | — |
| 30 min | 5.1% | 5.9% | 7.5% | 10.6% | 70.9% |
| 1 h | 2.1% | 3.9% | 7.8% | 12.4% | 73.8% |

Example 2

Diallyl Disulfide and Elemental Sulfur (as $S_8$) in a 2:1 Molar Mixture

A 10 mL round bottomed flask containing sublimed sulfur ($S_8$, 1.28 g, 5 mmol) was placed in an oil bath pre-heated to 120° C. When all of the sulfur had melted into a clear, straw-coloured liquid, diallyl disulfide (1.48 g, 10.1 mmol) was added all at once to the magnetically stirred liquid. Within three minutes, the initial cloudy two-layer liquid mixture became a clear, homogeneous solution with only one liquid layer. Stirring was continued at 120° C. for one hour. An aliquot was analyzed by $^1$H NMR and showed doublets for the $CH_2$—S protons at $\delta$ 3.09/3.07 (8% $All_2S$), $\delta$ 3.33/3.31 (9% $All_2S_2$), $\delta$ 3.50/3.48 (12% $All_2S_3$), $\delta$ 3.58/3.56 (16% $All_2S_4$), $\delta$ 3.62/3.60 (54% $All_2S_n$), $n \geq 5$.

Figure 3:
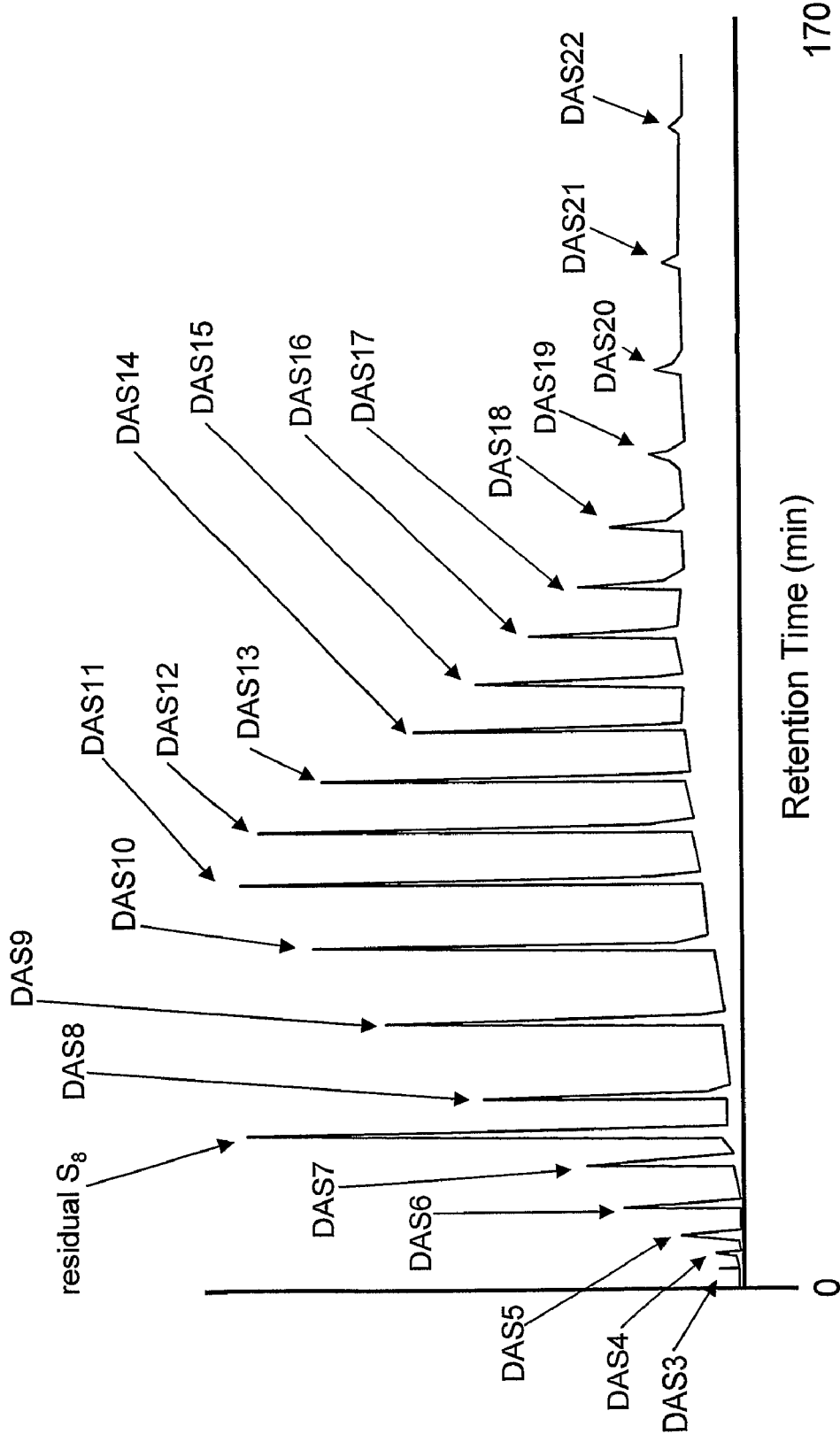
FIG. 3 is a graph of a HPLC analysis of a reaction product described in Example 2.

A 0.1081 g portion of the reaction product was washed with ethanol (5×1 mL) until the ethanol extract became colourless. Traces of solvent were removed from the residue to give 0.0291 g (27% yield) of an odorless, sticky yellow liquid, which was characterized by NMR and HPLC as a mixture of n=8 to 20 (see FIG. 3) showing the ethanol-insoluble fraction of the reaction products. Thus the $^1$H NMR spectrum showed a doublet for the $CH_2$—S protons at $\delta$ 3.62 and 3.60, which is characteristic of $All_2S_n$, $n \geq 5$. HPLC analysis showing the following approximate composition (uncorrected for systematically varying UV extinction coefficients, whereby the detector is increasingly sensitive to the higher polysulfides; hence the following results exaggerate the levels of the higher polysulfides): $All_2S_4$ (tr), $All_2S_5$ (1%), $All_2S_6$ (2%), $All_2S_7$ (4%), $All_2S_8$ (8%), $All_2S_9$ (11%), $All_2S_{10}$ (13%), $All_2S_{11}$ (13%), $All_2S_{12}$ (11%), $All_2S_{13}$ (9%), $All_2S_{14}$ (7%), $All_2S_{15}$ (6%), $All_2S_{16}$ (4%), $All_2S_{17}$ (3%), $All_2S_{18}$ (3%), $All_2S_{19}$ (2%), $All_2S_{20}$ (1%), $All_2S_{21}$ (tr), $All_2S_{22}$ (tr); elemental sulfur appears as a peak between those of $All_2S_7$ and $All_2S_8$.

Of the original 0.1081 g of reaction product, 0.0291 g was ethanol insoluble and 0.0703 g was ethanol soluble. The difference between the sum of the ethanol soluble and ethanol insoluble fractions, 0.0994 g and the original reaction product, 0.1081 g, represents volatile compounds (such as diallyl sulfide) lost in the work up and evaporation of ethanol. The recovery was 92.0%. The concentrated ethanol extract corresponded to $All_2S_n$, n=1 to 9, with HPLC analysis showing the following approximate composition (uncorrected for systematically varying UV extinction coefficients, whereby the detector is increasingly sensitive to the higher polysulfides; hence the following results exaggerate the levels of the higher polysulfides): $All_2S_2$ (2.3%), $All_2S_3$ (8.6%), $All_2S_4$ (17.3%), $All_2S_5$ (28.5%), $All_2S_6$ (23.7%), $All_2S_7$ (11.9%), $All_2S_8$ (5.3%), $All_2S_9$ (2.3%). Analysis of the ethanol soluble fraction by $^1$H NMR indicated 6.8% DAS2, 15.0% DAS3, 20.2% DAS4, and 58.0% DASn, $n \geq 5$. Analysis of the ethanol insoluble fraction showed a doublet at 3.62/3.60 indicating DASn, $n \geq 5$ as the only compounds present.

In a similar manner to the above extraction with ethanol, a 0.1063 g portion of the crude product was extracted with methanol (5×1 mL) until the methanol extract became colourless. Both the methanol extract and the residue from methanol extraction were freed from methanol using a rotary evaporator giving 0.0603 (G) methanol soluble fraction and 0.0404 g (38%) of an odorless, sticky yellow liquid residue. The overall recovery was 94.7%. Analysis of the methanol soluble fraction by $^1$H NMR indicated 8.7% DAS2, 20.1% DAS3, 38.0% DAS4, and 33.2% DASn, $n \geq 5$. Analysis of the methanol insoluble fraction showed a doublet at 3.62/3.60 indicating DASn, $n \geq 5$ as the only compounds present.

For the ethanol soluble extract, the HPLC analysis was as follows:

| Retention Time (min) | Peak Area (% Total) | Peak Identity |
|---|---|---|
| 3.9 | 2.3 | DAS2 |
| 5.2 | 8.5 | DAS3 |
| 6.8 | 17.1 | DAS4 |
| 9.5 | 28.1 | DAS5 |
| 13.6 | 23.5 | DAS6 |
| 19.8 | 11.7 | DAS7 |
| 23.7 | — | $S_8$ |
| 28.9 | 5.3 | DAS8 |
| 39.5 | 2.3 | DAS9 |
| 49.9 | 0.9 | DAS10 |
| 59.0 | 0.4 | DAS11 |

For the ethanol insoluble extract, the HPLC analysis was as follows:

| Retention Time (min) | Peak Area (% Total) | Peak Identity |
|---|---|---|
| 9.3 | 0.49 | DAS5 |
| 13.4 | 1.57 | DAS6 |
| 19.5 | 2.96 | DAS7 |
| 23.3 | 10.72 | $S_8$ |
| 28.6 | 6.04 | DAS8 |

-continued

| Retention Time (min) | Peak Area (% Total) | Peak Identity |
| --- | --- | --- |
| 39.1 | 8.95 | DAS9 |
| 49.7 | 10.00 | DAS10 |
| 58.8 | 10.59 | DAS11 |
| 66.3 | 8.77 | DAS12 |
| 73.2 | 7.30 | DAS13 |
| 80.1 | 5.83 | DAS14 |
| 86.8 | 4.97 | DAS15 |
| 93.4 | 3.46 | DAS16 |
| 100.3 | 2.75 | DAS17 |
| 108.5 | 2.27 | DAS18 |
| 118.5 | 1.63 | DAS19 |
| 130.9 | 0.93 | DAS20 |
| 146.2 | 0.57 | DAS21 |
| 165.1 | 0.30 | DAS22 |

For the methanol soluble extract, the HPLC was as follows:

| Retention Time (min) | Peak Area (% Total) | Peak Identity |
| --- | --- | --- |
| 3.9 | 2.8 | DAS2 |
| 5.2 | 11.3 | DAS3 |
| 6.8 | 25.8 | DAS4 |
| 9.5 | 32.3 | DAS5 |
| 13.7 | 16.0 | DAS6 |
| 19.9 | 7.1 | DAS7 |
| 23.8 | — | $S_8$ |
| 29.2 | 2.9 | DAS8 |
| 39.8 | 1.2 | DAS9 |
| 50.3 | 0.41 | DAS10 |
| 59.4 | 0.19 | DAS11 |

For the methanol insoluble extract, the HPLC was as follows:

| Retention Time (min) | Peak Area (% Total) | Peak Identity |
| --- | --- | --- |
| 6.3 | 1.7 | DAS4 |
| 8.9 | 1.5 | DAS5 |
| 13.1 | 3.9 | DAS6 |
| 19.2 | 7.1 | DAS7 |
| 23.2 | — | $S_8$ |
| 28.5 | 10.5 | DAS8 |
| 39.2 | 12.0 | DAS9 |
| 49.9 | 13.2 | DAS10 |
| 59.2 | 13.1 | DAS11 |
| 66.7 | 10.0 | DAS12 |
| 73.7 | 7.73 | DAS13 |
| 80.6 | 5.68 | DAS14 |
| 87.4 | 4.22 | DAS15 |
| 94.0 | 2.97 | DAS16 |
| 101.1 | 2.22 | DAS17 |
| 109.5 | 1.87 | DAS18 |
| 119.9 | 1.32 | DAS19 |
| 132.7 | 0.71 | DAS20 |
| 148.8 | 0.39 | DAS21 |

Example 3

Diallyl Disulfide and Elemental Sulfur (as $S_8$) in 1:1 Molar Ratio with Internal Standard A 10 mL round bottomed flask containing sublimed sulfur ($S_8$, 0.640 g, 2.50 mmol) was placed in an oil bath pre-heated to 120° C. When all of the sulfur had melted into a clear, straw-coloured liquid, a solution of 4,4'-di-tert-butylbiphenyl (0.0361 g, 0.136 mmol) in diallyl disulfide (0.365 g, 2.50 mmol) was added all at once to the magnetically stirred liquid. The 4,4'-di-tert-butylbiphenyl acts solely as an internal standard for analysis purposes. Within three minutes, the initial cloudy two-layer liquid mixture became a clear, homogeneous solution with only one liquid layer. A small amount of sample was withdrawn from the reaction mixture for analysis at various time points, e.g. 5 min, 30 min, 1 h, 1.5 h, and 2 h. The withdrawn samples were dissolved in $CDCl_3$ permitting both NMR and reversed phase HPLC analysis to be performed on the same sample. As desired, the remaining material could be directly used or the methanol- or ethanol-soluble fraction separated by extraction from the alcohol insoluble residue, which could then be dissolved in chloroform for further use.

Typical data from $^1$H NMR analysis at 500 MHz (relative to internal standard) showing the percentage of each homologue produced over time is given below:

| Time | DAS1 | DAS2 | DAS3 | DAS4 | ≧DAS5 |
| --- | --- | --- | --- | --- | --- |
| 0 min | 11.8% | 80.7% | 7.5% | — | — |
| 5 min | 10.0% | 66.5% | 7.2% | 2.7% | 13.7% |
| 10 min | 8.2% | 39.3% | 7.5% | 8.0% | 37.1% |
| 20 min | 6.5% | 12.4% | 9.0% | 12.3% | 59.8% |
| 30 min | 4.2% | 6.9% | 9.7% | 13.9% | 65.3% |
| 45 min | 2.4% | 4.9% | 10.3% | 14.6% | 67.7% |
| 1 h | 1.9% | 4.9% | 9.7% | 15.7% | 67.8% |
| 1.5 h | 2.1% | 4.6% | 9.8% | 15.5% | 68.2% |
| 2 h | 2.8% | 4.5% | 9.0% | 15.4% | 68.3% |

At the end of 2 hours heating the total area of the polysulfide fraction relative to that of the internal standard had decreased continuously to 68% of the original value, indicating some loss of volatile materials.

The HPLC analysis of a 30 minute aliquot was as follows:

| Retention Time (min) | Peak Area (% Total) | Peak Identity |
| --- | --- | --- |
| 3.8 | 0.6 | DAS2 |
| 5.0 | 2.0 | DAS3 |
| 6.6 | 4.1 | DAS4 |
| 9.1 | 6.4 | DAS5 |
| 13.2 | 9.6 | DAS6 |
| 19.2 | 8.6 | DAS7 |
| 23.0 | — | $S_8$ |
| 28.1 | 8.7 | DAS8 |
| 36.3 | — | Internal standard |
| 38.5 | 8.4 | DAS9 |
| 49.0 | 7.7 | DAS10 |
| 58.2 | 7.3 | DAS11 |
| 65.6 | 6.4 | DAS12 |
| 72.5 | 5.8 | DAS13 |
| 79.3 | 5.1 | DAS14 |
| 85.9 | 4.2 | DAS15 |
| 92.5 | 3.5 | DAS16 |
| 99.3 | 3.0 | DAS17 |
| 107.2 | 2.7 | DAS18 |
| 116.8 | 2.5 | DAS19 |
| 128.7 | 1.3 | DAS20 |
| 143.2 | 1.3 | DAS21 |
| 161.8 | 0.8 | DAS22 |

Example 4

Diallyl Disulfide and Elemental Sulfur (as $S_8$) in a 1:0.25 Molar Ratio

A 10 mL round-bottomed flask containing sublimed sulfur ($S_8$, 0.25 g, 0.977 mmol) was placed in an oil bath pre-heated to 120° C. When all of the sulfur had melted into a clear, straw-coloured liquid, diallyl disulfide (0.57 g, 3.90 mmol) was added all at once to the magnetically stirred liquid. Within three minutes, the initial cloudy two-layer liquid mixture became a clear, homogeneous solution with only one liquid layer. A small amount of sample was withdrawn from the reaction mixture for analysis at various time points, e.g. 0 min, 30 min, 1 h, 2 h, and 3 h. The withdrawn samples were dissolved in CDCl$_3$ permitting both NMR and reversed phase HPLC analysis to be performed on the same sample. The $^1$H NMR analysis at various time points (as above) is given below:

| Time | DAS1 | DAS2 | DAS3 | DAS4 | ≧DAS5 |
|---|---|---|---|---|---|
| 0 min | 10.90% | 78.30% | 8.60% | trace | trace |
| 30 min | 9.00% | 60.10% | 10.20% | 5.90% | 14.80% |
| 1 h | 7.00% | 38.9 | 13.40% | 12.70% | 28.00% |
| 2 h | 3.60% | 16.7 | 17.90% | 19.30% | 42.40% |
| 3 h | 2.00% | 13.5 | 18.20% | 19.80% | 45.00% |

The HPLC analysis of a three hour aliquot was as follows:

| Retention Time (min) | Peak Area (% Total) | Peak Identity |
|---|---|---|
| 3.7 | 2.2 | DAS2 |
| 5.0 | 8.1 | DAS3 |
| 6.6 | 9.5 | DAS4 |
| 9.3 | 13.2 | DAS5 |
| 13.5 | 13.2 | DAS6 |
| 19.7 | 11.1 | DAS7 |
| 23.6 | — | S$_8$ |
| 28.9 | 9.4 | DAS8 |
| 39.6 | 7.7 | DAS9 |
| 50.1 | 5.2 | DAS10 |
| 59.2 | 6.4 | DAS11 |
| 66.7 | 3.8 | DAS12 |
| 73.7 | 2.8 | DAS13 |
| 80.6 | 2.1 | DAS14 |
| 87.4 | 2.0 | DAS15 |
| 93.9 | 0.6 | DAS16 |
| 101.1 | 1.0 | DAS17 |
| 109.5 | 0.8 | DAS18 |
| 119.8 | 0.6 | DAS19 |
| 132.5 | 0.3 | DAS20 |

Example 5

Diallyl Sulfide with Elemental Sulfur (as S$_8$) in a 1:0.6 Molar Ratio

Under the above conditions a mixture of diallyl sulfide (bp 139-140° C.) and elemental sulfur as S$_8$ in a 1:0.6 molar ratio remained as two layers after two hours with no indication of reaction. Since the reaction conditions were well below the boiling point, it is concluded that the sulfur of diallyl sulfide is insufficiently reactive to open the S$_8$ ring under the conditions used for diallyl disulfide.

Example 6

Bis-(2-methallyl) Disulfide and Elemental Sulfur (as S$_8$) in a 1:1.1 Molar Ratio with Internal Standard A 10 mL round bottomed flask containing sublimed sulfur (S$_8$, 0.640 g, 2.50 mmol) was placed in an oil bath pre-heated to 120° C. When all of the sulfur had melted into a clear, straw-coloured liquid, a solution of 4,4'-di-tert-butylbiphenyl (0.0308 g, 0.116 mmol) in bis-(2-methylallyl) disulfide (0.415 g, 2.38 mmol) was added all at once to the magnetically stirred liquid. Within three minutes, the initial cloudy two-layer liquid mixture became a clear, homogeneous solution with only one liquid layer. A small amount of sample was withdrawn from the reaction mixture for analysis at various time points, e.g. 5 min, 10 min, 20 min, 30 min, 45 min, 1 h, 1.5 h, and 2 h. The withdrawn samples were dissolved in CDCl$_3$ permitting both NMR and reversed phase HPLC analysis to be performed on the same sample. As desired, the remaining material could be directly used or the methanol- or ethanol-soluble fraction separated by extraction from the alcohol insoluble residue, which could then be dissolved in chloroform for further use. The starting disulfide showed a singlet in its $^1$H NMR spectrum at δ 3.2638 for the two CH$_2$SS protons. After heating with sulfur, singlets were also found at δ 3.007 (monosulfide), 3.431 (trisulfide), 3.502 (tetrasulfide) and 3.537 (pentasulfide and higher). HPLC analysis (see Table) after heating for 30 min showed more than 20 evenly spaced peaks suggestive of a family of bis(2-methyl-2-propenyl) polysulfides analogous to those formed from diallyl disulfide.

Data from $^1$H NMR analysis showing progress of the reaction to the higher homologues is given below:

| Time | S*$_1$ | S$_2$ | S$_3$ | S$_4$ | ≧S$_5$ |
|---|---|---|---|---|---|
| 0 min | 5.1% | 90.9% | 3.9% | | |
| 5 min | 4.3% | 53.9% | 7.5% | 6.2% | 28.2% |
| 10 min | 4.0% | 12.8% | 11.3% | 14.0% | 57.8% |
| 20 min | 3.3% | 5.7% | 9.9% | 14.0% | 67.3% |
| 30 min | 2.8% | 5.5% | 10.1% | 14.7% | 66.9% |
| 45 min | 2.0% | 5.5% | 9.7% | 14.3% | 68.6% |
| 1 h | 1.6% | 5.1% | 11.4% | 14.6% | 68.5% |
| 2 h | 4.1% | 12.8% | 11.4% | 14.0% | 57.8% |

*S$_1$ = bis(2-methyallyl) sulfide;
S$_2$ = bis(2-methyallyl) disulfide;
S$_3$ = bis(2-methyallyl) trisulfide; etc.

Data from HPLC analysis of the 30 min sample is given below:

| Retention Time (min) | Peak Area (%) | Peak Identity |
|---|---|---|
| 6.0 | — | (CH$_2$=CMeCH$_2$)$_2$S$_2$ |
| 8.4 | — | (CH$_2$=CMeCH$_2$)$_2$S$_3$ |
| 11.3 | 5.0 | (CH$_2$=CMeCH$_2$)$_2$S$_4$ |
| 16.1 | 8.4 | (CH$_2$=CMeCH$_2$)$_2$S$_5$ |
| 24.0 | — | S$_8$ + (CH$_2$=CMeCH$_2$)$_2$S$_6$ |
| 33.5 | 10.8 | (CH$_2$=CMeCH$_2$)$_2$S$_7$ |
| 37.5 | — | Internal standard |
| 44.1 | 10.9 | (CH$_2$=CMeCH$_2$)$_2$S$_8$ |
| 54.4 | 10.2 | (CH$_2$=CMeCH$_2$)$_2$S$_9$ |
| 62.6 | 9.3 | (CH$_2$=CMeCH$_2$)$_2$S$_{10}$ |
| 69.7 | 8.2 | (CH$_2$=CMeCH$_2$)$_2$S$_{11}$ |
| 76.7 | 7.3 | (CH$_2$=CMeCH$_2$)$_2$S$_{12}$ |
| 83.5 | 6.1 | (CH$_2$=CMeCH$_2$)$_2$S$_{13}$ |
| 90.2 | 5.4 | (CH$_2$=CMeCH$_2$)$_2$S$_{14}$ |
| 96.9 | 4.4 | (CH$_2$=CMeCH$_2$)$_2$S$_{15}$ |
| 104.5 | 3.7 | (CH$_2$=CMeCH$_2$)$_2$S$_{16}$ |
| 113.8 | 3.0 | (CH$_2$=CMeCH$_2$)$_2$S$_{17}$ |
| 125.2 | 2.4 | (CH$_2$=CMeCH$_2$)$_2$S$_{18}$ |
| 139.5 | 2.0 | (CH$_2$=CMeCH$_2$)$_2$S$_{19}$ |
| 157.0 | 1.6 | (CH$_2$=CMeCH$_2$)$_2$S$_{20}$ |
| 178.9 | 1.3 | (CH$_2$=CMeCH$_2$)$_2$S$_{21}$ |

Example 7

Garlic Oil and Elemental Sulfur (as $S_8$) in a 1:1.1 Molar Ratio

A 10 mL round-bottomed flask containing sublimed sulfur ($S_8$, 0.6414 g, 2.505 mmol) was placed in an oil bath preheated to 120° C. When all of the sulfur had melted into a clear, straw-coloured liquid, commercial garlic oil (0.4191 g, 2.35 mmol based on diallyl trisulfide) was added all at once to the magnetically stirred liquid (garlic oil is a mixture of about 80% diallyl polysulfides and 20% allyl methyl polysulfides). Within three minutes, the initial cloudy two-layer liquid mixture became a clear, homogeneous solution with only one liquid layer. A small amount of sample was withdrawn from the reaction mixture after 30 min and dissolved in $CDCl_3$ for analysis by both NMR and reversed phase HPLC. HPLC analysis, shown below indicated formation of a large number of polysulfides including compounds with retention times similar to those of $DAS_n$, n=7-19.

| Retention Time (min) | Peak Area (%) | Peak Identity |
|---|---|---|
| 4.1 | 2.7 | |
| 5.1 | 2.4 | |
| 5.2 | 2.3 | |
| 5.7 | 1.7 | |
| 6.2 | 1.1 | |
| 6.6 | 3.1 | |
| 7.2 | 3.3 | |
| 7.8 | 2.7 | |
| 8.7 | 1.5 | |
| 9.1 | 4.4 | |
| 10.1 | 4.2 | |
| 11.3 | 3.5 | |
| 12.6 | 1.9 | |
| 13.3 | 7.1 | |
| 14.8 | 5.4 | |
| 16.6 | 3.3 | |
| 18.3 | 2.2 | |
| 19.5 | 6.3 | DAS7 |
| 22.0 | 3.6 | |
| 23.7 | — | Sulfur |
| 28.8 | 2.8 | DAS8 |
| 32.1 | 1.8 | |
| 39.5 | 2.7 | DAS9 |
| 43.1 | 1.7 | |
| 50.2 | 2.7 | DAS10 |
| 53.8 | 2.0 | |
| 59.4 | 3.0 | DAS11 |
| 62.5 | 1.9 | |
| 66.9 | 2.5 | DAS12 |
| 70.1 | 1.8 | |
| 73.9 | 3.0 | DAS13 |
| 77.5 | 1.8 | |
| 81.0 | 2.4 | |
| 84.7 | 1.8 | |
| 87.8 | 2.2 | DAS14 |
| 91.8 | 1.6 | |
| 94.4 | 1.9 | DAS15 |
| 99.1 | 1.1 | |
| 101.6 | 1.4 | DAS16 |
| 110.3 | 1.1 | DAS17 |
| 120.9 | 1.0 | DAS18 |
| 133.9 | 0.9 | DAS19 |
| 170.9 | 1.2 | |

NMR spectroscopic analysis of the $CH_2S$ protons indicated formation of families of diallyl polysulfides as well as allyl/methyl polysulfides, $MeS_nCH_2CH=CH_2$, with 65% of the product having n≧5 compared to 11% for the original garlic oil. NMR analysis of the $CH_3S$ protons indicated formation of 62% of families of methyl allyl polysulfides having $CH_3S_n$, n≧5 compared to 16% for the original garlic oil.

| Time | $S^*_1$ | $S_2$ | $S_3$ | $S_4$ | ≧$S_5$ |
|---|---|---|---|---|---|
| 0 min | 27.5% | 23.6% | 23.7% | 14.1% | 11.0% |
| 30 min | 8.2% | 8.4% | 8.9% | 9.4% | 65.2% |

*$S_1$ = allyl sulfides;
$S_2$ = allyl disulfides;
$S_3$ = allyl trisulfides; etc.

Figure 4:
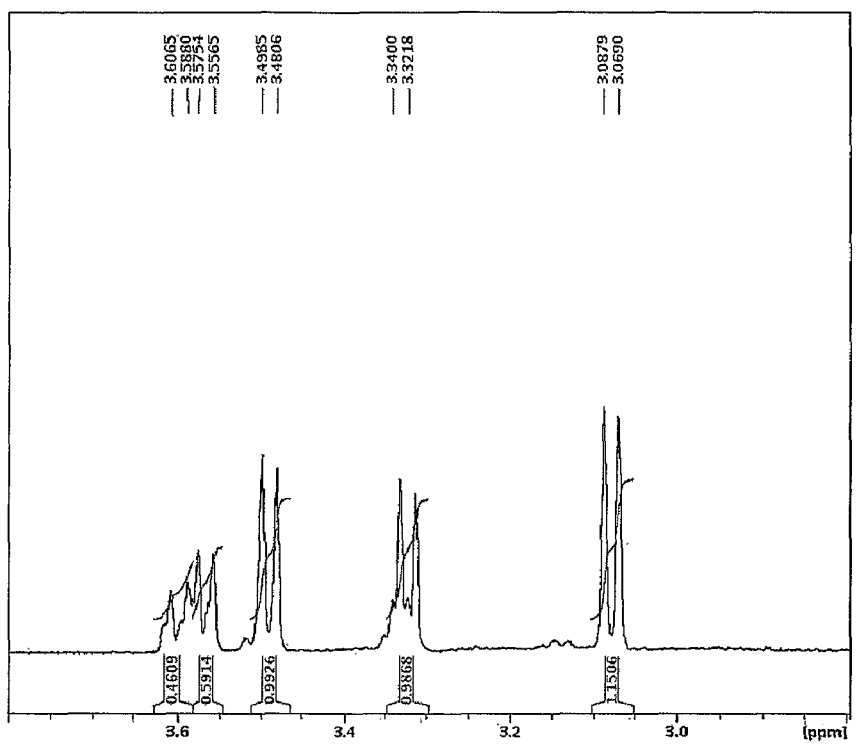
FIG. 4 is a graph of a NMR spectrum of a starting material described in Example 7.
Figure 5:
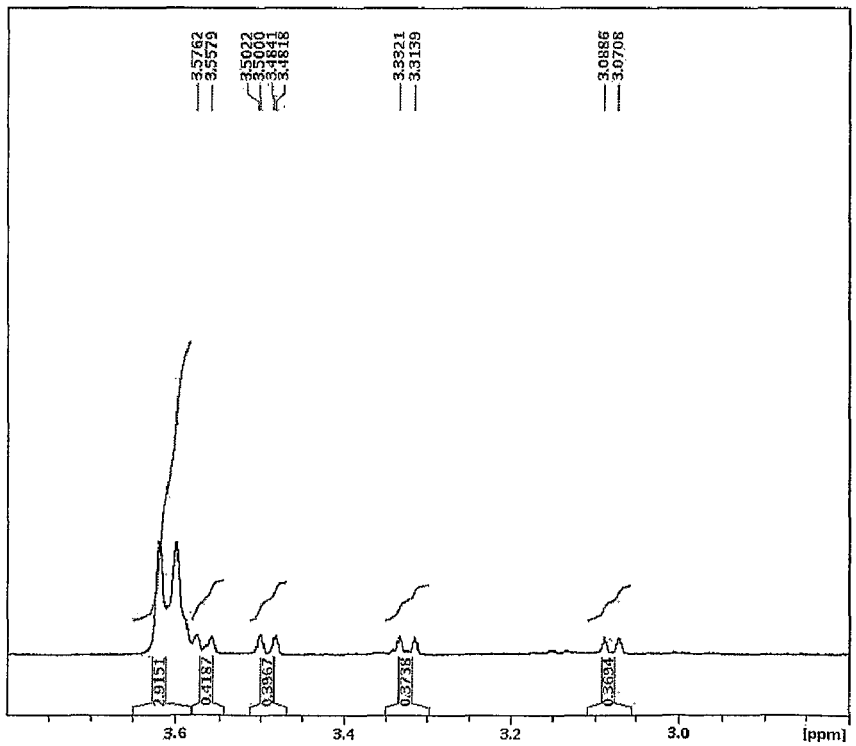
FIG. 5 is a graph of a NMR spectrum of 0.5 hr sample described in Example 7.

Comparison of the $^1$NMR spectrum of the starting material (FIG. 4) with the 0.5 hr sample (FIG. 5) clearly shows the increase in size of the doublet for the $CH_2$—S protons at δ3.62 and 3.60, characteristic of $All_2S_n$, n≧5, together with a corresponding decrease in size of the doublets for lower S-chain length polysulfides.

Example 8

2-cyclohexen-1-yl Disulfide and Elemental Sulfur (as $S_8$) in a 1:1 Molar Ratio at 120° C.

A 10 mL round-bottomed flask containing sublimed sulfur ($S_8$, 0.256 g, 1.00 mmol) was placed in an oil bath pre-heated to 120° C. When all of the sulfur had melted into a clear, straw-coloured liquid, 2-cyclohexen-1-yl disulfide (0.226 g, 1.00 mmol) was added all at once to the magnetically stirred liquid. Within three minutes, the initial cloudy two-layer liquid mixture became a clear, homogeneous solution with only one liquid layer. A small amount of sample was withdrawn from the reaction mixture for analysis at various time points, e.g., 5 min, 30 min, 1 h and 2 h. The withdrawn samples were dissolved in $CDCl_3$ permitting both NMR and reversed phase HPLC analysis to be performed on the same sample. HPLC analysis, tabulated below, shows a progression of peaks for the 2-cyclohexen-1-yl polysulfides through that with 18 sulfur atoms in a chain. In its $^1$H NMR spectrum 2-cyclohexen-1-yl disulfide shows a multiplet at δ 3.48-3.51 which can be assigned to the allylic CH—S proton. Upon heating, a new broad peak, absent in the starting material, appears at δ 3.88. This peak is assumed to be the allylic CH—$S_n$ protons of 2-cyclohexen-1-yl polysulfides. From integration of the several NMR spectra the time course of polysulfide formation is shown below:

| | Time (min) | | | | |
|---|---|---|---|---|---|
| | 0 | 5 | 30 | 60 | 120 |
| 2-cyclohexen-1-yl disulfide | 100% | 95% | 66% | 38% | 15% |
| 2-cyclohexen-1-yl polysulfides | 0% | 5% | 33% | 62% | 85% |

Data from HPLC analysis of the 1 h sample is given below:

| Retention Time (min) | Peak Area (%) | Peak Identity |
|---|---|---|
| 13.9 | 5.7 | (cyclohexen-1-yl)$_2S_2$ |
| 23.2 | — | $S_8$ + (cyclohexen-1-yl)$_2S_3$ |
| 30.7 | 4.2 | (cyclohexen-1-yl)$_2S_4$ |
| 41.9 | 7.0 | (cyclohexen-1-yl)$_2S_5$ |
| 52.7 | 8.7 | (cyclohexen-1-yl)$_2S_6$ |

-continued

| Retention Time (min) | Peak Area (%) | Peak Identity |
|---|---|---|
| 62.0 | 11.2 | $(cyclohexen-1-yl)_2S_7$ |
| 69.9 | 9.9 | $(cyclohexen-1-yl)_2S_8$ |
| 77.6 | 9.0 | $(cyclohexen-1-yl)_2S_9$ |
| 85.2 | 9.1 | $(cyclohexen-1-yl)_2S_{10}$ |
| 92.5 | 8.6 | $(cyclohexen-1-yl)_2S_{11}$ |
| 100.0 | 7.0 | $(cyclohexen-1-yl)_2S_{12}$ |
| 109.0 | 5.3 | $(cyclohexen-1-yl)_2S_{13}$ |
| 120.0 | 4.7 | $(cyclohexen-1-yl)_2S_{14}$ |
| 133.7 | 4.0 | $(cyclohexen-1-yl)_2S_{15}$ |
| 150.6 | 2.5 | $(cyclohexen-1-yl)_2S_{16}$ |
| 171.6 | 2.3 | $(cyclohexen-1-yl)_2S_{17}$ |
| 198.0 | 1.1 | $(cyclohexen-1-yl)_2S_{18}$ |

HPLC analysis was terminated after the $(cyclohexen-1-yl)_2S_{18}$ peak, but higher homologues are expected, by analogy with Examples 2 and 3.

Example 9

Diallyl Disulfide and Elemental Sulfur (as $S_8$) in a 1:0.2 Molar Ratio at 130° C.

Diallyl disulfide (20 g; 0.14 moles) was mixed with powdered sulfur (8 g, 0.03 moles), and heated to 130° C. for 10 minutes, and then cooled. An ethanol extraction was performed on the resultant mixture, thereby solubilising the lower chain length polysulfides. The ethanolic extract was analyzed by HPLC, with the following results:

| Retention Time (min) | Peak Area (%) | Peak Identity |
|---|---|---|
| 6.0 | 2.8 | DAS |
| 7.3 | 12.1 | DAS2 |
| 9.8 | 10.7 | DAS3 |
| 13.6 | 24.3 | DAS4 |
| 19.5 | 20.8 | DAS5 |
| 28.6 | 10.7 | DAS6 |
| 42.0 | 14.1 | DAS7 |

Example 10

Diallyl Disulfide and Elemental Sulfur (as $S_8$) in a 1:0.2 Molar Ratio at 110° C.

Diallyl disulfide (20 g; 0.14 moles) was mixed with powdered sulfur (8 g, 0.03 moles), and heated to 110° C. for 10 minutes, and then cooled. An ethanol extraction was performed on the resultant mixture, thereby solubilising the lower chain length polysulfides. The ethanolic extract was analyzed by HPLC, with the following results:

| Retention Time (min) | Peak Area (%) | Peak Identity |
|---|---|---|
| 6.0 | 3.9 | DAS |
| 7.3 | 34.4 | DAS2 |
| 9.9 | 10.0 | DAS3 |
| 13.6 | 15.3 | DAS4 |
| 19.6 | 12.0 | DAS5 |
| 28.6 | 6.3 | DAS6 |
| 42.0 | 14.0 | DAS7 |

Example 11

Diallyl Disulfide and Elemental Sulfur (as $S_8$) in a 1:0.4 Molar Ratio at 145° C.

Diallyl disulfide (20 g; 0.14 moles) was mixed with powdered sulfur (12 g; 0.05 moles), and heated to 145° C. for 5 minutes, and then cooled. An ethanol extraction was performed on the resultant mixture, thereby solubilising the lower chain length polysulfides. The ethanolic extract was analyzed by HPLC, with the following results:

| Retention Time (min) | Peak Area (%) | Peak Identity |
|---|---|---|
| 6.0 | 2.9 | DAS |
| 7.2 | 3.8 | DAS2 |
| 9.8 | 9.0 | DAS3 |
| 13.5 | 19.9 | DAS4 |
| 19.4 | 24.0 | DAS5 |
| 28.4 | 12.6 | DAS6 |
| 41.6 | 13.0 | DAS7 |

Figure 6:
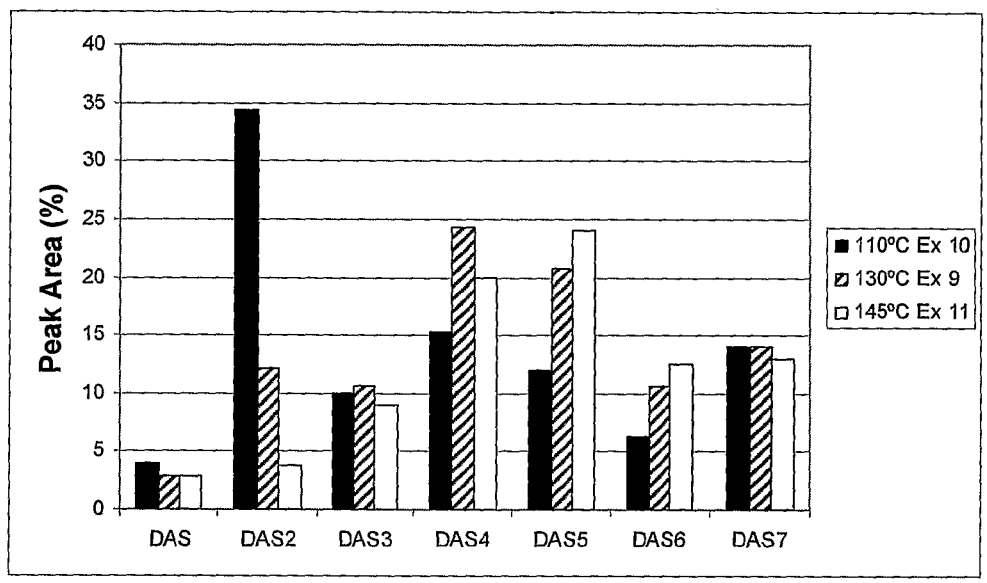
FIG. 6 is a graph summarizing the results of Examples 9-11.

FIG. 6 summarises the results of Examples 9-11, and illustrates the effect of reaction temperature on the spectrum of polysulfides produced. It can be seen that as the reaction temperature is varied from 110° C. through to 145° C., the spectrum of diallyl polysulfides produced is shifted towards the longer chain lengths. Thus, temperature may be used to control the spectrum of chain length. At the lower temperature of Example 10, a substantial amount of unreacted DAS2 remained.

Example 12

Diallyl Disulfide and Elemental Sulfur (as $S_8$) in a 1:0.4 Molar Ratio at 110° C. and then 140° C.

Diallyl disulfide (20 g; 0.14 moles) was mixed with powdered sulfur (16 g, 0.06 moles), heated to 110° C. and held there for 15 minutes. The reaction mixture was then cooled until a sulfur precipitate appeared, and then reheated to 140° C., held there for 5 minutes, and then cooled. An ethanol extraction was performed on the resultant mixture, thereby solubilising the lower chain length polysulfides. The ethanolic extract was analyzed by HPLC, with the following results:

| Retention Time (min) | Peak Area (%) | Peak Identity |
|---|---|---|
| 6.0 | 2.1 | DAS |
| 7.2 | 4.8 | DAS2 |
| 9.8 | 9.0 | DAS3 |
| 13.6 | 27.8 | DAS4 |
| 19.5 | 22.1 | DAS5 |
| 28.5 | 12.1 | DAS6 |
| 41.9 | 19.0 | DAS7 |

It can be seen in this example, very little unreacted DAS2 remains (less than 5% by peak area), and the higher polysulfides (DAS4-DAS7) comprise some 80% of the total peak area, by comparison with some 64% higher polysulfides in Example 10. In addition, the DAS4 concentration in Example 12 was nearly 1.5 times higher than that obtained in Example 10 as a consequence of the reaction conditions.

Significant advantage may therefore be obtained by use of such a two-temperature regime reaction, i.e. mixing the starting reagents (elemental sulfur and diallyl polysulfide, e.g. DAS2, or 2-substituted analogue thereof); heating to above the triple point of sulfur; holding the mixture at that temperature; reducing the temperature until a sulfur precipitate is observed; and re-heating the mixture to above the sulfur triple point.

Nomenclature
DAS Diallyl sulfide
DAS2 Diallyl disulfide
DAS3 Diallyl trisulfide
DAS4 Diallyl tetrasulfide
DAS5 Diallyl pentasulfide
DAS6 Diallyl hexasulfide
DAS7 Diallyl heptasulfide
DASn Diallyl $S_n$

REFERENCES (1) (a) Polysulfides as biologically active ingredients of garlic. Münchberg, U.; Anwar, A.; Mecklenburg, S.; Jacob, C. *Org. Biomol. Chem.* 2007, 5, 1505-18. (b) Diallyl trisulfide suppresses the proliferation and induces apoptosis of human colon cancer cells through oxidative modification of β-tubulin. Hosono, T.; Fukao, T.; Ogihara, J.; Ito, Y.; Shiba, H.; Seki, T. *J. Biol. Chem.* 2005, 280, 41487-41493.

(2) Nematocides containing essential oils of plants for controlling pine wood nematode in environment-friendly method, or nematocidal compounds extracted from the same. Park, Ill. Kwon; Shin, Sang Chul, Repub. Korean Kongkae Taeho Kongbo (2007), CODEN: KRXXA7 KR 2007035319 A 20070330, Application: KR 2005-90018 20050927.

(3) Composition containing organic polythioether compounds used as pesticide. Luo, Shanfeng, Faming Zhuanli Shenqing Gongkai Shuomingshu (2007), 11 pp. CODEN: CNXXEV CN 1985591 A 20070627, Application: CN 1015-5154 20061208 [*Chemical Abstracts* Number 147: 183068, AN 2007:710044].

(4) Insecticidal principles of garlic. Banerji, Asoke; Amonkar, Shanker Vasudev. Indian (1978), 10 pp, CODEN: INXXAP IN 144278 A1 19780422, Application: IN 75-BO344 19751127 [*Chemical Abstracts* Number 92:17188, AN 1980:17188].

(5) Phenolic compounds as antioxidants for lubricants. Braid, Milton, U.S. (1985), 5 pp., CODEN: USXXAM U.S. Pat. No. 4,551,259 A, 19851105, Application: US 83-561411 19831214 [*Chemical Abstracts* Number 104:168116, AN 1986:168116].

(6) Pesticidal garlic composition for foliar applications. Arand, Anthony; Arand, John K. U.S. (2003), 21 pp., CODEN: USXXAM, U.S. Pat. No. 6,511,674 B1 20030128, Application: US 98-99480 19980617. [*Chemical Abstracts* Number 138:102386, AN 2003:71735].

(7) Diallyl polysulfides from garlic as insecticides and acaricides. Gaudout, David; Inisan, Claude; DURECHOU, Serge; Megard, Denis. Fr. Demande (2005), 20 pp. CODEN: FRXXBL FR 2863144 A1 20050610 [*Chemical Abstracts* Number 143:2646, AN 2005:492122].

(8) Use of garlic extract for systematic treatment of growing crops. Struth, Hugh, Brit. UK Pat. Appl. (2005), CODEN: BAXXDU GB 2414912 A 20051214 AN 2005:1303053.

(9) Allylic sulfides as tickicides. Ferrando, Jorge Alberto Santiago. Belg. (1986), 14 pp. CODEN: BEXXAL BE 903756 A1 19860602, Application: BE 85-11393 19851202. [*Chemical Abstracts* Number 105:218898, AN 1986:618898].

(10) Garlic oil and/or its components for withering prevention and activation of plants. Kominato, Yutaka; Takeyama, Yoshimori; Nishimi, Tomoyuki, Jpn. Kokai Tokkyo Koho (1999), 4 pp., CODEN: JKXXAF JP 11222410 A 19990817 Heisei. Application: JP 98-38038 19980203. [*Chemical Abstracts Number* 131:154761, AN 1999:518658].

(11) Sulfides as plant dormancy-inhibiting agents. Kominato, Jo; Nishimura, Shoji; Takeyama, Yoshimori., Jpn. Kokai Tokkyo Koho (1995), 3 pp. CODEN: JKXXAF JP 07126108 A 19950516 Heisei. Application: JP 91-289044, 19910814. [*Chemical Abstracts* Number CAN 123:77166, AN 1995:712191].

(12) Nonaqueous electrolyte for a lithium secondary battery. Kim, Jin-sung. U.S. Pat. Appl. Publ. (2004), 9 pp. CODEN: USXXCO US 2004265702 A1 20041230, Application: US 2004-869437 20040617. Priority: KR 4255-7 20030627. [*Chemical Abstracts* Number 142:97467, AN 2005:1959].

(13) Amine-free corrosion inhibitors for metal protection in industrial aqueous systems. Crovetto, Rosa; Kupper, Robert J., U.S. Pat. Appl. Publ. (2005), 4 pp. CODEN: USXXCO US 2005079095 A1 20050414, Application: US 2003-682693, 20031009. [*Chemical Abstracts Number* 142:395990, AN 2005:325490].

(14) Cyclodextrin inclusion compound of garlicin, its preparations and preparation method. Mao, Youchang; Mao, Xiaomin., Faming Zhuanli Shenqing Gongkai Shuomingshu (2005), 7 pp., CODEN: CNXXEV CN 1565430 A 20050119 Application: CN 2003-124592 20030622.

(15) Polysulfides as lipid peroxidation inhibitors. Awazu, Shoji; Horie, Toshiharu; Kodera, Yukihiro; Nagae, Shinji; Matsuura, Hiromichi; Itakura, Yoichi, Eur. Pat. Appl. (1992), 10 pp. CODEN: EPXXDW EP 464521 A2 19920108, Designated States R: DE, FR, GB, NL. Application: EP 91-110268 19910621. Priority: JP 90-165445 19900622. [*Chemical Abstracts* Number 116:136231 AN 1992:136231].

(16) Sulfides as deoxyglucosone formation inhibitors. Nagata, Tadahiro; Hosoda, Hiroshi; Sakagami, Kazuyuki. Jpn. Kokai Tokkyo Koho (2007), 17 pp. CODEN: JKXXAF JP 2007261983 A 20071011, Application: JP 2006-87918 20060328. [*Chemical Abstracts* Number 147: 426110, AN 2007:1146248].

(17) Sulfuration process and catalysts for the preparation of diorgano trisulfides from organo halides and sulfur. Sinha, Pradipta; Roy, Sujit. U.S. Pat. Appl. Publ. (2002), 6 pp. CODEN: USXXCO US 2002198410 A1 20021226 Application: US 2001-820202 20010328 [Chemical Abstracts Number 138:55663, AN 2002:978493].

(18) Copper(II)/Tin(II) Reagent for Allylation, Propargylation, Alkylation, and Benzylation of Disulfides and Elemental Sulfur: New Insight into the "Copper Effect". Sinha, Pradipta; Kundu, Abhijit; Roy, Sujit; Prabhakar, Sripadi; Vairamani, M.; Sankar, A. Ravi; Kunwar, A. C. Organometallics (2001), 20(1), 157-162.

(19) Synthesis of diallyl mono- and polysulfides. Chu, Yong; Zhao, Min-zheng; Xu, Ming-xia. *Hecheng Huaxue* (2001), 9(6), 541-542. [*Chemical Abstracts* Number 137:325137, AN 2002:130041].

(20) Process for producing of synthetic alliaceous ethereal oil. Lellei, Gabor; Szalay, Pal; Havalda, Gyula. (Hung.). Hung. Pat. Appl. (2000), 16 pp. CODEN: HUXXCV HU 9802619 A1 20000628, Application: HU 98-9802619, 19981111 [*Chemical Abstracts* Number 147:257585, AN 2007:928466].

(21) Manufacture of synthetic garlic essential oil. Szalay, Pal; Lellei, Gabor; Szalay, Karoly; Havalda, Gyula. Hung. Pat. Appl. (1998), 16 pp. CODEN: HUXXCV HU 9700287 A119981130, Application: HU 97-9700287 19970131. [*Chemical Abstracts* Number 147:196730, AN 2007:203143].

(22) Trisulfides and tetrasulfides from Bunte salts. Milligan, Brian; Saville, B.; Swan, J. M. *Journal of the Chemical Society* (1963), 3608-14.

(23) Sulfur linkage in vulcanized rubber. Reaction of methyl iodide with sulfur compounds. Selker, M. L., *Journal of Industrial and Engineering Chemistry* (1948), 40, 1467-70.

(24) Organic polysulfides. II. The action of anhydrous potassium pentasulfide on allyl iodide and on some aromatic halogen compounds. Thomas, J. S.; Riding, R. W. *Journal of the Chemical Society, Transactions* (1924), 125, 2214-9.

(25) Thiosulfoxides. The intermediates in rearrangement and reduction of allylic disulfides. Höfle, G.; Baldwin, J. E. *J. Am. Chem. Soc.* 1971, 93, 6307-8.

(26) Sulphur compounds. Part 140. Structures and relative stabilities of seven isomeric forms of $H_2S_2O_2$. Steudel, R.; Miaskiewicz, K. *J. Chem. Soc. Dalton Trans,* 1991, 2395-2399.

(27) Exchange of parts between molecules at equilibrium. V. Alkyl-terminated chain polysulfides and polyselenides. Grant, D.; Van Wazer, J. R. *J. Am. Chem. Soc.* 1964, 86, 3012-3017.

(28) Reaction of allylic thioethers with elemental sulfur. Baechler, R. B.; Hummel, J. P.; Mislow, K. *J. Am. Chem. Soc.* 1973, 95, 4442-4.

(29) Sulfur compounds, 212. Preparation of organic polysulfanes $R_2S_n$ (n=5, 7, 8, 9) from sulfenyl chlorides, RSCl, and transition metal polysulfido complexes. Steudel, R.; Hassenberg, K.; Münchow, V.; Schumann, O.; Pckardt, J. *Eur. J. Inorg. Chem.* 2000, 921-8.

(30) Aversion of European starlings (*Sturnus vulgaris*) to garlic oil treated granules: Garlic oil as an avian repellent. Garlic oil analysis by nuclear magnetic resonance spectroscopy. Hile, A. G.; Shan, Z.; Zhang, S.-Z.; Block, E. *J. Agric. Food Chem.* 2004, 52, 2192-6.

The invention claimed is:

1. A compound of formula:

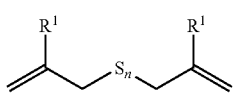

where n is from 3 to 22; and
$R^1$ is selected from the group comprising:
   hydrogen;
   phenyl;
   carboethoxy;
   carbomethoxy;
   carboxy;
   hydroxymethyl;
   trimethylsilylmethyl;
   short-chain alkyl, with 2, 3 or 4 carbon atoms;
   chloro; and
   fluoro;
provided that when n is from 3 to 8, $R^1$ is not hydrogen.

2. A compound, according to claim 1, of formula:

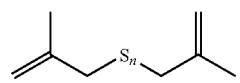

where n is from 9 to 22.

3. A process for extending the sulfur chain length of diallylic polysulfides, comprising 2 or more sulfur atoms, selected from the group comprising:
   bis(2-propenyl)polysulfides; and
   bis(2-substituted-2-propenyl)polysulfides;
comprising the steps of mixing said diallylic polysulfide with elemental sulfur and heating the mixture to a temperature in excess of 50° Celsius.

4. A process according to claim 3 wherein said mixture is heated to a temperature at or in excess of the melting point of elemental sulfur.

5. A process according to claim 3 wherein said diallylic polysulfide comprises diallyl polysulfide.

6. A process for extending the sulfur chain length of diallylic polysulfides, comprising 2 or more sulfur atoms, selected from the group comprising:
   bis(2-propenyl)polysulfides; and
   bis(2-substituted-2-propenyl)polysulfides;
said process comprising the steps of mixing said diallylic polysulfide with molten sulfur.

7. A process according to claim 3 wherein said diallylic polysulfides comprise polysulfides having fewer than 22 sulfur atoms.

8. A compound, according to claim 1, of formula:

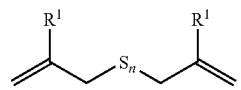

where $R^1$ is selected from the group comprising:
   phenyl;
   carboethoxy;
   carbomethoxy;
   carboxy;
   hydroxymethyl;
   trimethylsilylmethyl;
   short-chain alkyl, with 2, 3 or 4 carbon atoms;
   chloro; and
   fluoro;
and n is from 3 to 20.

9. A compound of formula:

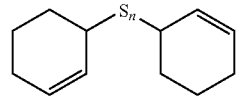

where n is from 3 to 18.

10. A method of producing a compound according to claim 9 comprising the step of mixing 2-cyclohexen-1-yl disulfide with molten sulfur.

11. A compound of formula:

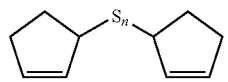

where n is from 3 to 18.

12. A method of producing a compound according to claim 11 comprising the step of mixing 2-cyclopenten-1-yl disulfide with molten sulfur.

13. A process for extending the sulfur chain length of allyl methyl polysulfides ($MeS_nCH_2CH=CH_2$) where $n \geq 2$, comprising the steps of mixing said allyl methyl polysulfides with elemental sulfur and heating the mixture to a temperature in excess of 50° Celsius.

14. A process according to claim 13 wherein said mixture is heated to a temperature at or in excess of the melting point of elemental sulfur.

15. A process for extending the sulfur chain length of allyl methyl polysulfides ($MeS_nCH_2CH=CH_2$) where $n \geq 2$, comprising the step of mixing said allyl methyl polysulfides with molten sulfur.

* * * * *